United States Patent
Deck et al.

(10) Patent No.: US 9,642,725 B2
(45) Date of Patent: May 9, 2017

(54) SYSTEM AND METHOD FOR JOINT TESTING

(71) Applicant: Advanced Mechanical Technology, Inc., Watertown, MA (US)

(72) Inventors: Joseph F. Deck, Somerville, MA (US); Bradley L. Hunter, Lexington, MA (US); Bruce F. White, Boston, MA (US)

(73) Assignee: Advanced Mechanical Technology, Inc., Watertown, MA (US)

( * ) Notice: Subject to any disclaimer, the term of this patent is extended or adjusted under 35 U.S.C. 154(b) by 407 days.

(21) Appl. No.: 14/532,664

(22) Filed: Nov. 4, 2014

(65) Prior Publication Data

US 2015/0057809 A1 Feb. 26, 2015

Related U.S. Application Data

(63) Continuation-in-part of application No. 13/295,610, filed on Nov. 14, 2011, now Pat. No. 9,351,857.

(51) Int. Cl.
| | |
|---|---|
| *A61F 2/76* | (2006.01) |
| *G05B 15/02* | (2006.01) |
| *G06N 99/00* | (2010.01) |
| *A61F 2/46* | (2006.01) |
| *G09B 23/32* | (2006.01) |
| *A61F 2/38* | (2006.01) |

(52) U.S. Cl.
CPC ............... *A61F 2/76* (2013.01); *A61F 2/468* (2013.01); *G05B 15/02* (2013.01); *G06N 99/005* (2013.01); *G09B 23/32* (2013.01); *A61F 2/38* (2013.01); *A61F 2002/7695* (2013.01)

(58) Field of Classification Search
CPC ... A61F 2/38; A61F 2/76; A61F 2/468; G05B 15/02; G06N 99/005; G09B 23/32
See application file for complete search history.

(56) References Cited

U.S. PATENT DOCUMENTS

| | | | |
|---|---|---|---|
| 7,823,460 B2 | 11/2010 | White | |
| 2004/0254771 A1* | 12/2004 | Riener | G09B 23/32 703/7 |
| 2005/0134561 A1 | 6/2005 | Tierling et al. | |

(Continued)

OTHER PUBLICATIONS

Victoria Richardason, Analysis of a Lower Limb Prosthesis, Apr. 24, 2008, Worcester Polytechnic Institute.

(Continued)

*Primary Examiner* — Dennis M Butler
(74) *Attorney, Agent, or Firm* — AKC Patents, LLC; Aliki K. Collins

(57) ABSTRACT

The present invention relates to joint simulators, and in particular, to methods and systems for controlling joint simulators by using a haptic mapping technique. A joint simulator is used to closely approximate the conditions within the body, particularly with respect to human and animal joints, and can be used to test and evaluate prosthetics for use in various parts of a human or animal body. The haptic mapping technique improves the rate of convergence of the actual testing forces to the prescribed forces during repetitive performance and life testing. The method is used in conjunction with an impedance-mode servo controller.

26 Claims, 11 Drawing Sheets

Simulator Controller 100

(56) References Cited

U.S. PATENT DOCUMENTS

| | | | |
|---|---|---|---|
| 2007/0051180 A1* | 3/2007 | White | A61F 2/468 73/760 |
| 2007/0270685 A1 | 11/2007 | Kang et al. | |
| 2011/0118878 A1 | 5/2011 | White | |
| 2011/0257764 A1* | 10/2011 | Herr | A61F 2/60 623/24 |
| 2012/0123592 A1 | 5/2012 | Carignan et al. | |

OTHER PUBLICATIONS

S.P. Chan et al., Robust Impedance Control of Robot Manipulators, International Journal of Robotics and Automation, 1991, pp. 222-227, vol. 6 No. 4, ACTA Press, Anaheim, CA.

ISO 10328:2006, Prosthetics—Structural Testing of Lower-Limb Prostheses—Requirements and Test Methods, Oct. 1, 2006.

\* cited by examiner

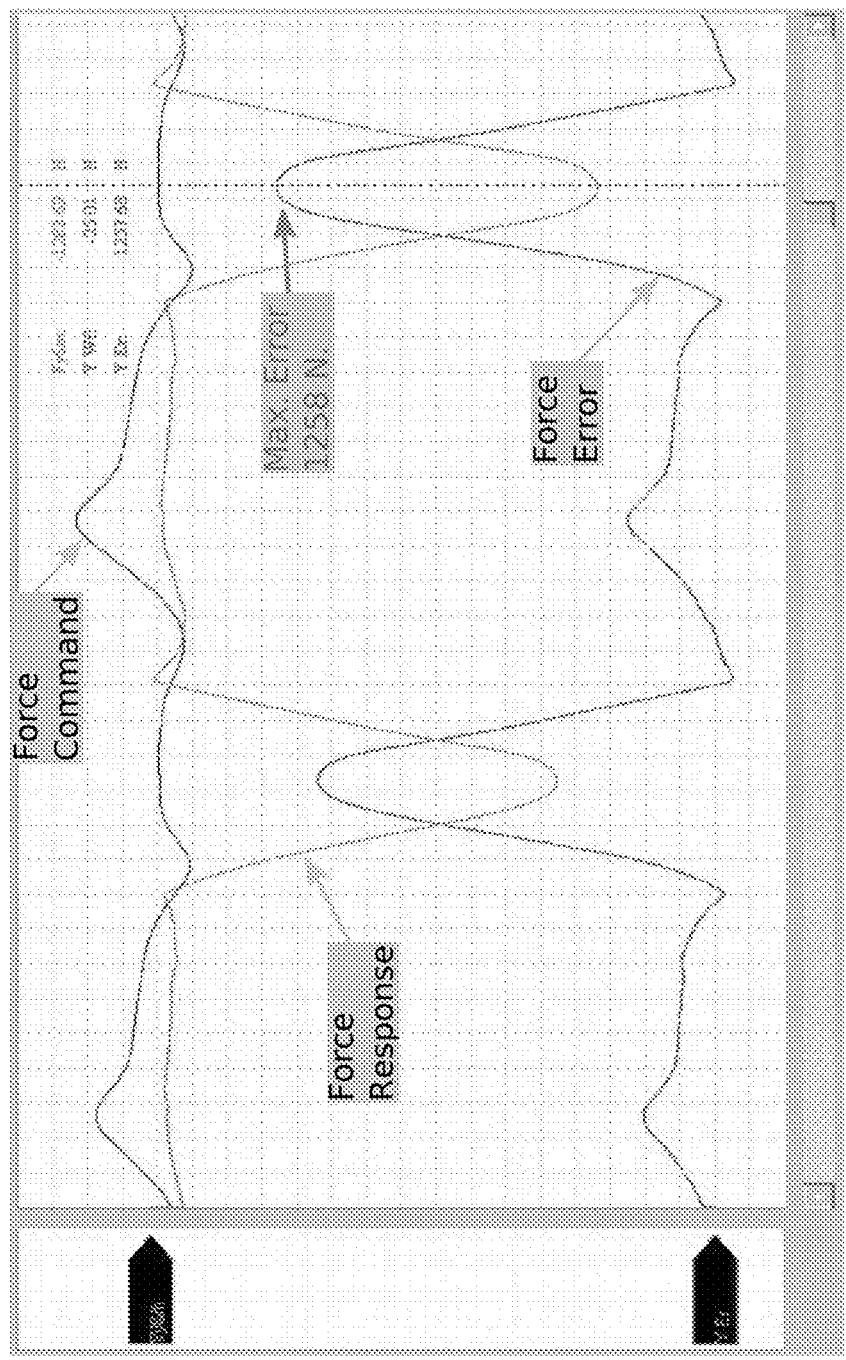
FIG. 6A  Initial Response, No Haptic Mapping

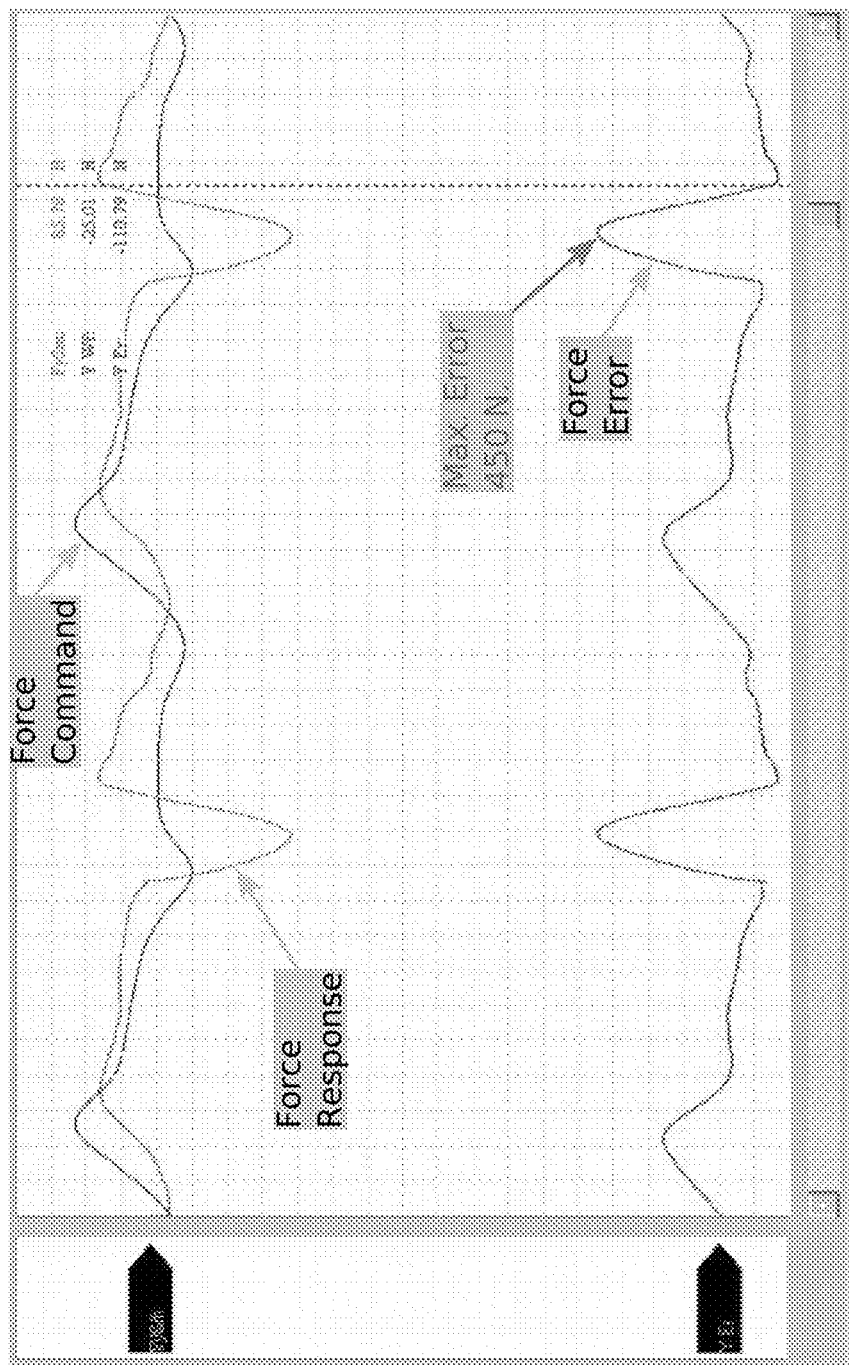
FIG.6B Initial Response, Using Haptic Mapping

Response After 20 Cycles, Using Haptic Mapping

SYSTEM AND METHOD FOR JOINT TESTING

CROSS REFERENCE TO RELATED CO-PENDING APPLICATIONS

This application is a continuation in part and claims the benefit of U.S. application Ser. No. 13/295,610 filed on Nov. 14, 2011 and entitled METHOD AND APPARATUS FOR JOINT MOTION SIMULATION which is commonly assigned and the contents of which are expressly incorporated herein by reference.

FIELD OF THE INVENTION

The present invention relates to a system and a method for joint testing, and more particularly to joint testing wherein a haptic map is used to improve the rate of convergence of the actual testing forces to the prescribed forces. The invention has application to machines used for cyclic testing of biological and prosthetic joints.

BACKGROUND OF THE INVENTION

Standardized testing of prostheses usually involves various tests that are designed to assess the mechanical and physical characteristics of a prosthesis. Typical tests include static proof tests, static failure tests and cyclic tests. Static proof tests assess the structural strength of the prosthesis by applying specified loads to the prosthesis according to a particular standard. Static failure tests also assess the structural strength of the prosthesis, but in this case, the maximum force applied before failure occurs is recorded. Cyclic tests are the most relevant tests for fatigue testing. In a cyclic test, the prosthesis is placed in a testing machine and testing forces are applied at a specified frequency (cyclic repetition rate) according to a particular test regimen. The desired frequency is often in the range of 1.3 Hz to 0.5 Hz (0.8 to 2 seconds period). Cyclic fatigue tests typically run for hundreds of thousands to millions of cycles.

Similar tests are also applied to natural biological joints, such as human or animal knees, hips, ankles, shoulders, and elbows, among others, for research purposes. Testing live subjects can present practical difficulties and often is morally unacceptable, so the majority of such testing is performed on joints from cadavers or animal carcasses. Such cadaveric testing is often called "in vitro" testing. Some typical testing goals are research into the kinematics, constraint behavior, and pathologies of natural joints. Cyclic testing is also useful in such studies.

The invention applies to cyclic joint testing using joint simulator machines. In the field of the invention, such machines are referred to using a variety of phrases such as "prosthesis testing machine," "prosthetic joint simulator," "testing machine," "joint simulator" and the like. Such a machine is in many cases suitable for testing either biological or prosthetic joints, because often similar test protocols are applicable to both biological and prosthetic joints. The invention applies to a range of machines intended for the testing of biological joints, prosthetic joints, or both biological and prosthetic joints.

For brevity, in the remainder of this document, the term "joint" should be understood as applicable equally to a biological or prosthetic joint unless the term is specifically limited. Similarly, although specific discussions and examples may focus on a biological or a prosthetic joint in order to give concreteness, it should be understood that the application of such discussions and examples to either biological or prosthetic joints is within the scope of the invention.

The testing of a joint occurs according to a defined set of displacement and force commands. The term "force" includes both linear forces and rotational torques. Also, the term "displacement" includes both translational and rotational movements. In many cases, the commanded forces and displacements are defined in a test regimen produced by a recognized standards body, for example those prescribed by ISO or ASTM. In other cases the commanded forces and positions may arise from clinical observations, or from engineering study requirements. In almost all cases, the tested joint is modeled as a set of two or more rigid bodies with defined kinematic degrees of freedom. A typical testing machine is described in U.S. application Ser. No. 13/295,610 filed on Nov. 14, 2011 and entitled METHOD AND APPARATUS FOR JOINT MOTION SIMULATION, the contents of which are expressly incorporated herein by reference. The test waveform defines up to six axes of motion for each body and prescribes forces or displacements referenced to these axes. Performing the test includes operating the testing machine so that the forces and displacements it applies to the tested joint conform closely to those prescribed by the test waveform.

For a valid test, the actual testing forces and displacements applied to the joint should agree well with those prescribed by the test regimen. This requirement implies that the joint testing machine must be capable of frequency response commensurate with the demands of the test regimen. Fourier analysis reveals that the prescribed waveforms typically have spectral energy at frequencies considerably above the cyclic repetition frequency of the test, often at ten or higher harmonics of the repetition frequency. Intermittent contact between the parts of a joint is often encountered by prosthetic devices in service, and therefore its inclusion in the testing regimen is mandatory. Yet, intermittent contact is a particularly challenging condition to reproduce faithfully in a testing machine, because usually it is associated with near-impulsive forces having considerable high-frequency spectral content. A system that can improve the speed and accuracy with which actual test forces and displacements converge to the values prescribed by the test regimen is a useful addition to the field.

SUMMARY OF THE INVENTION

The present invention relates to joint simulator testing machines, and in particular, to methods and systems for controlling joint simulators by using a haptic mapping technique. A joint simulator is used to create conditions closely matching those within the body, particularly with respect to human and animal joints, and can be used to test and evaluate prosthetics for use in various parts of a human or animal body. Joint simulator machines are also very often used for research testing of biological human and animal joints. The haptic mapping system reduces initial errors and improves the rate of convergence of the actual testing forces to the prescribed forces during repetitive performance and life testing. The method is used in conjunction with an impedance-mode servo controller. The system and method are applicable to testing of prosthetic devices for the knees, hips, shoulders, elbows, spines, ankles, hearts or heart valves, or any other articulating components of a human or animal body. The system and method also are applicable to in vitro testing of natural biological joints.

In general, in one aspect, the invention features a system for a joint testing including a simulator stage, a drive system, a force sensor, a displacement sensor and a digital control system. The simulator stage includes first and second mounts configured to support first and second elements of a prosthetic joint device, respectively. The drive system is configured to apply testing forces and displacements to the first and second elements of the prosthetic joint device. The force sensor is configured to measure forces applied to the first and second elements of the prosthetic joint device. The displacement sensor is configured to measure displacements applied to the first and second elements of the prosthetic joint device. The digital control system is configured to control the drive system in response to inputs from a test waveform, the force sensor and the displacement sensor, so that the applied testing forces and displacements on the first and second elements of the prosthetic joint device are close to prescribed testing forces and displacements, respectively. The digital control system includes an impedance control topology, a waveform compensation system and an iterative learning control system (ILC) comprising a haptic mapping application.

Implementations of this aspect of the invention may include one or more of the following features. The haptic mapping application is configured to first generate a haptic map by performing force and displacement commands prescribed by the test waveform at a speed selected to allow servocontrollers to follow prescribed force and displacement waveforms with minimal amplitude attenuation and phase lag and to record positions of force-controlled axes, next to apply phase and amplitude pre-compensation to the generated haptic map to correct for anticipated drive system lag and attenuation in the recorded positions of the force-controlled axes, thereby generating a pre-compensated haptic map, and then to use the pre-compensated haptic map to initialize the ILC system. The haptic mapping application generates the haptic map by performing force and displacement commands prescribed by the test waveform at a speed in the range of 1/3 to 1/50 of a nominal speed. The waveform compensation system is configured to receive the test waveform and apply phase and amplitude compensation in order to generate a compensated waveform. The compensated waveform is used as an input to the drive system and comprises a modulated phase and a modulated amplitude and the modulated phase and modulated amplitude of the compensated waveform compensate for a phase lag and amplitude attenuation of the drive system so that the drive system output is close to the prescribed testing forces and displacements. The drive system includes one or more hydraulic actuators and the hydraulic actuators are controlled by electrically-actuated servo-valves. The impedance control topology includes a multi-axis compensator and a multi-axis position controller. The compensator is configured to receive a force error comprising a difference between the input from the force sensor and the prescribed testing forces and to convert the force error to a compensated position error by applying a compensation function to the force error. The position controller is configured to receive and correct the compensated position error. The position controller is configured to correct a position error comprising a difference between the input from the position sensor and the prescribed displacements. The compensation function comprises a proportional component and an integrating component. The ILC is configured to receive position errors and force errors and convert them into a frequency domain representation. The testing forces comprise linear and/or rotational forces. The displacements comprise translational and/or rotational displacements.

In general, in another aspect, the invention features a method for a joint testing including the following. First, providing a simulator stage comprising first and second mounts configured to support first and second elements of a prosthetic joint device, respectively. Next, providing a drive system configured to apply testing forces and displacements to the first and second elements of the prosthetic joint device. Next, providing a force sensor configured to measure forces applied to the first and second elements of the prosthetic joint device. Next, providing a displacement sensor configured to measure displacements applied to the first and second elements of the prosthetic joint device. Next, providing a digital control system configured to control the drive system in response to inputs from a test waveform, the force sensor and the displacement sensor, so that the applied testing forces and displacements on the first and second elements of the prosthetic joint device are close to prescribed testing forces and displacements, respectively. The digital control system comprises an impedance control topology, a waveform compensation system and an iterative learning control system (ILC) comprising a haptic mapping application.

The details of one or more embodiments of the invention are set forth in the accompanying drawings and description below. Other features, objects, and advantages of the invention will be apparent from the following description of the preferred embodiments, the drawings, and the claims.

BRIEF DESCRIPTION OF THE DRAWINGS

Referring to the figures, wherein like numerals represent like parts throughout the several views:

FIG. 6A through FIG. 6E are force vs. time plots showing the behavior and advantages of the haptic mapping system and method.

DETAILED DESCRIPTION OF THE INVENTION

The present invention relates to joint simulator machines, and in particular, to methods and systems for controlling such machines by using a haptic mapping technique. A joint simulator machine is used to closely approximate conditions within the body, particularly with respect to human and animal joints, and can be used to test and evaluate prosthetics for use in various parts of a human or animal body. It can also be used to test natural biological joints. The haptic mapping technique improves the rate of convergence of the actual testing forces to the prescribed forces during repetitive performance and life testing. The method is used in conjunction with an impedance-mode servo controller. The method is applicable to testing of prosthetic devices for the knees, hips, shoulders, elbows, spines, ankles, hearts or heart valves, or any other articulating components of a human or animal body. It is also applicable to testing of biological joints.

Description of Joint Simulator Machines

Figure 1A:
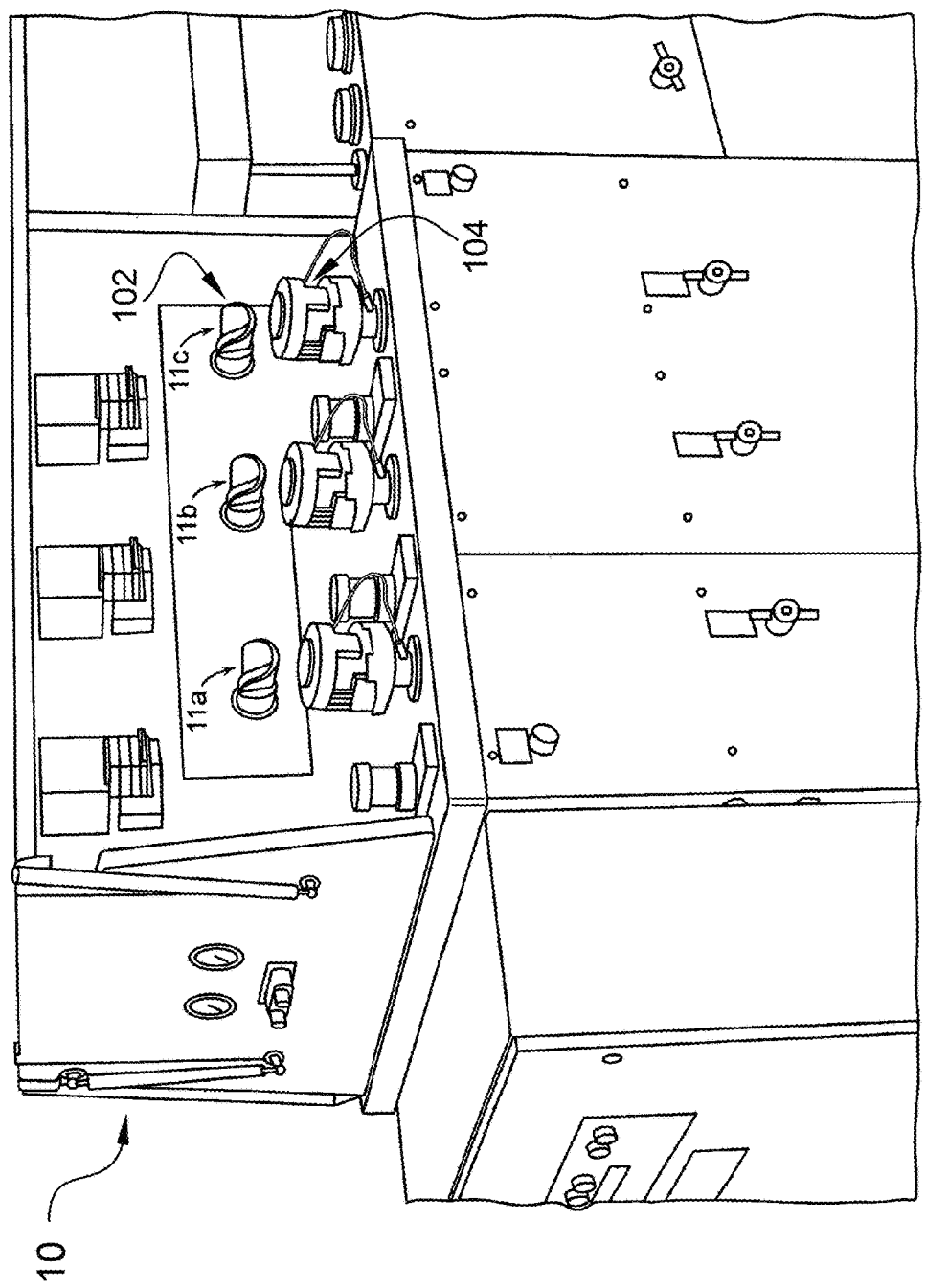
FIG. 1A illustrates a prosthetic simulator machine.
Figure 1B:
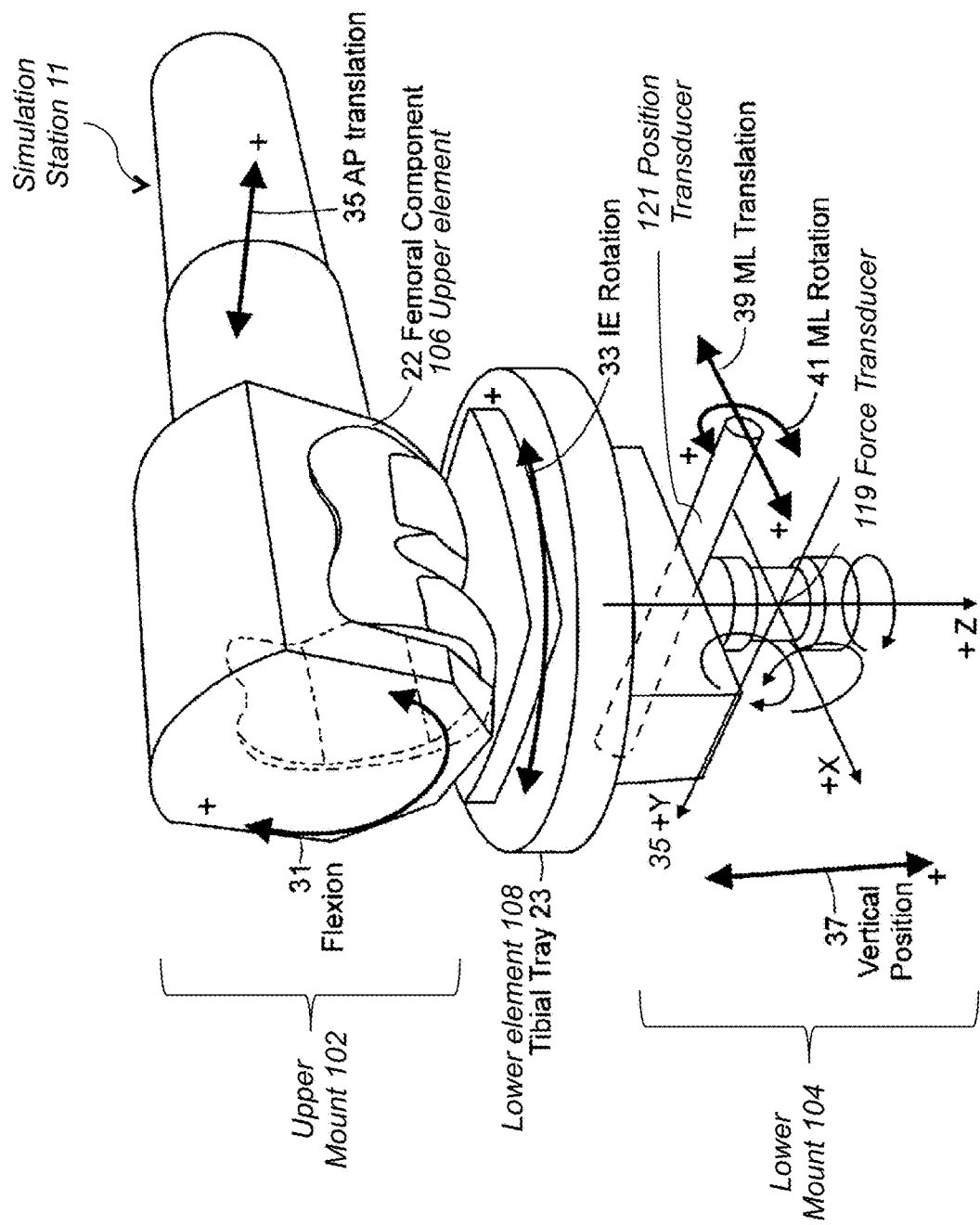
FIG. 1B depicts a schematic illustration of a simulator stage for a prosthetic device.

An exemplary embodiment of a joint simulator machine 10 is shown in FIG. 1A. The joint simulator is used to test joints in a manner that approximates the conditions within the human body. The simulator is preferably capable of performing "accelerated wear" tests, in which the prosthesis is put through a large number of cycles (e.g. 20 million cycles) of pre-determined motions that are likely to be encountered in the human body. In the embodiment shown in FIG. 1A, the simulator includes three stations 11a, 11b, and 11c, each having one or more actuators, such as servo-hydraulic actuators, for driving a prosthesis to simulate various types of body motions. It will be understood that a simulator according to the invention can have any number of stations and indeed we will shortly discuss a second exemplary embodiment comprising a single station. Also, although servo-hydraulic actuators are often used in joint simulator machines, the scope of the invention includes other types of actuators. For example, actuators may be based on linear electric motors or on rotary electric motors. One element of a joint to be tested is mounted into an upper mount 102 and the other element of the joint is mounted to a lower mount (platform) 104, as shown in FIG. 1B. The lower mount 104 is also referred to herein as the specimen stage or mechanical stage. The upper and lower mounts are rotatable and translatable with respect to each other along a multiplicity of directions, commonly called "axes" in the field. The relative motions of the upper and lower mounts produce displacements of the elements of the joint that are thereto mounted.

An example of a simulator station 11 for a prosthetic knee joint implant is shown schematically in FIG. 1B. FIG. 1B illustrates a prosthetic knee joint, although the system can carry elements for many kinds of joints. In the specific case of a knee prosthesis, the elements of the prosthetic device are the Femoral Component 22 and the Tibial Tray 23. However, more generally we refer to upper 106 and lower 108 elements of the device. The joint elements 106, 108 butt against each other between the two mounts and are separately driven through a programmed motion. A prior simulation system is described in the U.S. Pat. No. 7,823,460 to Bruce F. White, which is incorporated by reference in its entirety.

In one embodiment of a joint simulator, the upper mount 102 is moveable by actuators in the lateral Y direction 35 and is also rotatable 31 about a front to rear axis X with the angle α. The lower platform 104 is moveable in the Z axis 37 and is also rotatable 33 about the vertical Z axis through an angle θ. The simulator includes a multi-axis force/torque transducer 119 mounted beneath a lower device element 108 so that the six components of prosthetic contact force and moment can be monitored. Transducer 119 may be a six-channel strain gauge transducer. In addition, the system includes one or more position sensors or transducers 121 to measure the relative translational and rotational positions of the upper and lower components 106, 108 of the device. The position sensor 121 can monitor the flexion/extension angle 31, internal/external (IE) rotation angle 33, anterior/posterior (AP) translation 35, and vertical (compression/distraction) position 37 of the prosthesis. The medial-lateral (ML) knee translation 39 and varus valgus rotation 41 can also be monitored. The position sensor 121 may comprise multiple uniaxial position transducers so disposed as to measure the displacements and rotations of the actuators of the machine.

In another embodiment, the position sensor 121 outputs relative displacements of the upper 106 and lower 108 components of the prosthesis, either by direct measurement or by calculation from the positions of the several actuators.

In another embodiment of a joint simulator, the lower platform 104 is moveable in the X, Y and Z directions and is rotatable about the Z axis. The upper platform 102 is rotatable about a rotary axis parallel to the X axis. On the upper platform is carried a second moving element that is rotatable about an axis perpendicular to the X axis. This second moving element of the upper platform 102 carries the upper part of the prosthesis 106, providing an additional degree of freedom of motion that can extend the testing capabilities of the machine. For a knee prosthesis the additional degree of freedom provides control of the varus/valgus joint displacement. This embodiment may also incorporate force and position sensors similar to 119 and 121.

It will be evident from the foregoing discussion of two exemplary embodiments that the invention applies to a multiplicity of specific arrangements of actuators, including actuators that are carried on moving portions of the machinery. The actuators produce motion along their respective axes, where the axes of motion may be fixed with respect to the frame of the machine or the axes of motion may be moveable with respect to the frame of the machine. The multiple actuators and corresponding directions of motion are capable of producing relative displacement of the elements of the joint.

Description of Test Waveforms

As was mentioned above, a test waveform defines up to six axes of motion for each body and prescribes forces or displacements referenced to these axes. Performing the test includes operating the testing machine so that the forces and displacements it applies to the prosthesis conform as closely as possible to those prescribed by the test waveform. The prescribed forces and displacements in a prosthetic device test regimen have a cyclic repetition rate that is usually on the order of 1.3 to 0.5 Hz. (0.8 to 2 seconds period.) However, Fourier analysis reveals that the prescribed waveforms typically have spectral energy at many harmonics of the repetition rate. When the prescribed waveform includes intermittent contact between the parts of the prosthesis, near-impulsive forces with considerable high-frequency spectral energy are often encountered.

Figure 2:
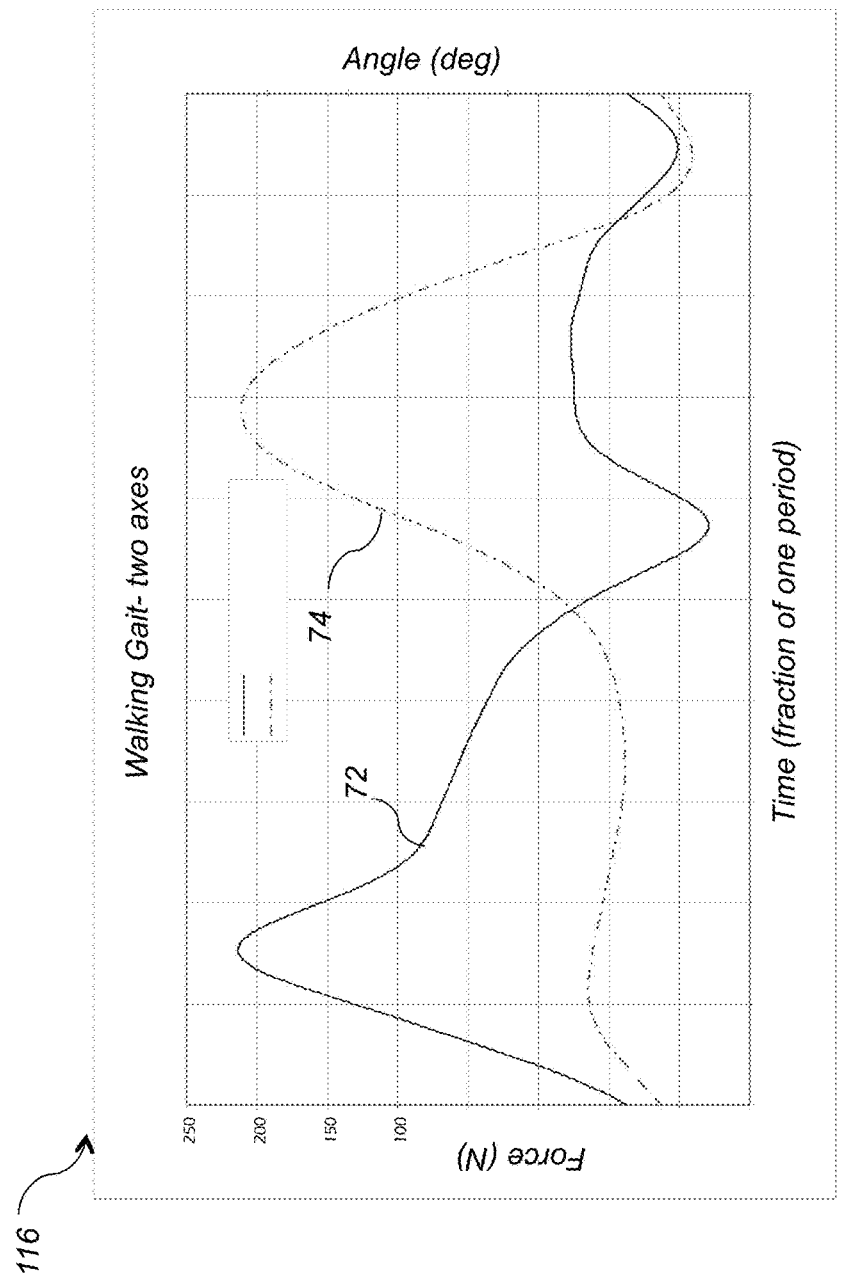
FIG. 2 illustrates testing waveforms outlining the flexion angle and AP (Anterior-Posterior) direction force for cyclic fatigue testing intended to simulate a typical walking gait.

A portion of one standardized test waveform is shown in FIG. 2. The curves in this figure are taken from a standardized waveform for the gait of a human subject having a prosthetic joint, published by the International Organization for Standardization (ISO) 14243. This test waveform is a practical testing regimen designed to simulate conditions during walking Referring to FIG. 2, the portions of the waveform 116 reproduced here are the flexion angle waveform 74 and the AP (Anterior-Posterior) force waveform 72. Flexion angle is shown on the right-hand ordinate axis and AP force is shown on the left-hand ordinate axis. The abscissa of FIG. 2 relates to time and to the progression of the gait cycle by assigning unit value to the cycle period. Fractions on the abscissa correspond to fractional progression through the cycle. For example if the full cycle corresponds to 800 milliseconds then the fraction 0.3 represents the waveform values at 240 milliseconds through the cyclic period. For this waveform, the flexion axis is in position control and the AP axis is in force control. The complete gait waveform is not reproduced here but comprises an additional four axes of control consisting of force or position waveforms for the ML (Medial-Lateral), DC (Distraction-Compression), VV (Varus-Valgus) and IE (Internal-External) axes. The names reference anatomical directions and are often employed in the field. In the most preferable embodiment of the joint simulator machine, each axis may be under force or position control according to the requirements of the waveform and the research objective.

The objective of a useful joint simulator is to exercise the device under test so that the applied forces and displacements agree closely with the command waveforms, two examples of which are shown in FIG. 2. Of course the waveforms appropriate for a given joint and a given test vary from the example of FIG. 2 according to the demands of the test and the characteristics of the joint.

Simulator Control System

Figure 3:
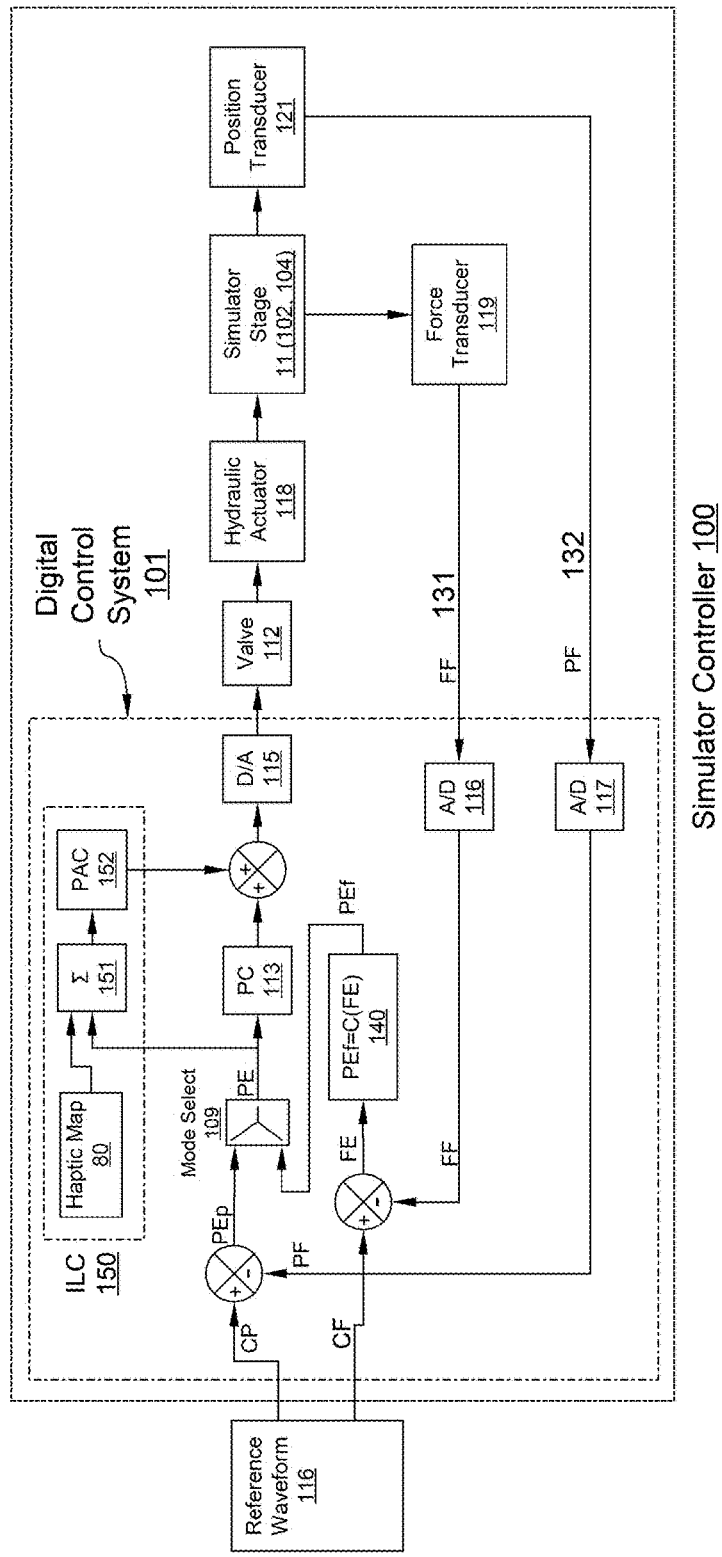
FIG. 3 is a schematic diagram of a control system according to this invention.

A schematic of a control system 100 for a joint simulator according to one embodiment is shown in FIG. 3. The simulator stage 11 is driven by one or more servo-hydraulic actuators 112, 118 under the control of a digital control system 101. As described in further detail below, the control system according to this embodiment includes an impedance control topology, a waveform compensation function 116, and an iterative learning control (ILC) system 150 incorporating a haptic mapping system 80.

As a rule of thumb, the characteristic frequency of a servocontroller should be approximately ten times the highest frequency present in the input waveform in order to assure good amplitude and phase fidelity of the output. However, as a practical matter, a servo control system meeting this specification while also capable of the speed and force levels required to accurately follow the high frequency content typical of prosthetic test waveforms would be difficult to design and expensive to build.

If the transfer function of a servo-controlled system is reasonably well known, the frequency bandwidth requirements can sometimes be relaxed through the use of phase and amplitude compensation (PAC) techniques 152. These techniques generate a compensated input from the prescribed waveform, and this compensated waveform becomes the actual input to the servocontroller. Relative to the prescribed trajectory, the compensated input is modulated in phase and amplitude in a way that is inverse to the phase lag and amplitude attenuation of the servo, such that the output of the servo-controlled axis is closer to the prescribed trajectory. This type of waveform compensation is inherently a non-causal feed-forward technique. The accuracy of the computed input compensation depends on an accurate and reliable characterization of the system's amplitude and phase response. Because of uncertainties in system identification and nonlinearities arising from several causes, inevitably the required compensation is known only approximately. The errors in the resulting performance of the test are usually still too large to be tolerated, and those errors must be measured and further reduced over the course of several cycles of the test waveform using a feedback technique, such as iterative learning control (ILC).

In ILC, response errors are measured for each axis. The error is a force or a position error, corresponding to the type of command required for the axis in a particular test. A control law is applied to these errors, then PAC to account for servocontroller dynamics, resulting in a compensation curve for every point of the trajectory for each axis. On the next iteration of the trajectory, these compensation curves are added with the previously-accumulated compensation to become feed-forward elements of the signals that drive the axis actuators. As suggested by the adjective "iterative," this process can be repeated on subsequent repetitions of the waveform to build up a better compensation curve, thus easing the requirement for accurate system identification in the control law that generates the compensation curve. ILC is a form of integral feedback control. However, because it is able to look at the errors over the span of an entire cycle of a waveform, and because the goal is to make every cycle of the trajectory identical to the commanded waveform, ILC is able to perform a look-ahead, or non-causal, compensation. This is a distinguishing feature compared to integral control action in a compensator, which always has a phase lag relative to the error signal. ILC is a way of combining non-causal PAC waveform compensation techniques with a feedback mechanism that reduces the sensitivity to system identification errors and plant nonlinearities.

In the preferred embodiment, the PAC technique is implemented in the frequency domain. Using the well-known technique of discrete Fourier transformation, the error signal may be represented as a group of mutually-orthogonal phase and amplitude coefficients in the frequency domain. It is then straightforward to apply inverse phase and magnitude compensation obtained from a previously-acquired frequency-domain characterization of the transfer function of the servocontrolled axis. The resulting frequency-domain compensation can then be converted to its time-domain representation and added to the source waveform to produce a compensated waveform. It is also possible to implement the PAC technique solely in the time domain and such an implementation is within the scope of the invention.

The discrete Fourier transform is a linear operation. Therefore it is mathematically equivalent for the ILC system to accumulate position errors before the PAC function, or instead to accumulate compensation waves after the PAC function. In other words, the accumulator block 151 may be placed before or after the PAC function. In FIG. 3 it is shown before the PAC function. In a preferred embodiment the accumulator may sum the frequency-domain representation of the error or the compensation. However it is also possible to implement the accumulator using the time-domain representation of error or the time-domain representation of compensation.

Because of their ability to deliver high forces in a compact and inexpensive package, hydraulic actuators 118 are often used in prosthesis testing machines. In the usual implementation, the actuator for an axis is controlled by an electrically-actuated servovalve 112. The servovalve 112 is a flow-control device, where the flow from the hydraulic pressure source into the actuator is (approximately) linearly related to the command voltage applied to the servovalve. For practical purposes, the sub-system comprising the pressure source, servovalve and actuator may be treated as a voltage to speed transducer, where the speed of the actuator is approximately equal to a constant times the voltage applied to the servovalve. That voltage, in turn, is typically the output of a digital control system 101, specifically from a digital-to-analog converter 115. The control system incorporates a feedback element—a force sensor 119, for a force-controlled axis, and/or a position sensor 121, for a position-controlled axis. The control system 101 attempts to modulate the servovalve drive signal so that at every time during a cycle of the test waveform 116, the measured force feedback (FF) 131 or position feedback (PF) 132 agree with the force or position that is prescribed for the test being run.

When an axis is to be a force-controlled axis, two controller topologies suggest themselves. In the first, the prescribed force 116 and the force feedback signal 131 are used directly to modulate the hydraulic pressure applied to the actuator 118. The position feedback 132 of the actuator is disregarded. The hydraulic pressure is related to the force or torque applied by the axis through the area of the actuator— piston area, for a linear actuator, or vane area, for a rotational actuator. It is possible to achieve an effective control of axis force by this method. However, the control method becomes complex when it must confront intermittent contact between the parts of the prosthesis. In this case, the physical plant exhibits an inherent extreme nonlinearity. Essentially zero force is developed over a large displacement until the prosthesis parts come into contact, and then force builds up very rapidly with small changes in displacement. Force error (FE), defined as the difference between the commanded force (CF) and the measured force (FF), requires a fundamentally different response depending on whether the parts are in contact or not. Out of contact, force error must produce a change in hydraulic flow so that the actuator position changes to bring the parts of the prosthesis into contact. In contact, force error must produce change in hydraulic pressure to regulate the contact force. This change of control strategy makes it difficult to tune the control system for both good performance and unconditional stability. Nonetheless, this topology has been used successfully in known testing machines.

A second controller topology is the impedance control. In this topology, the axis is always regarded as a position-controlled axis. Position is the integral of speed, and therefore position is approximately proportional to the integral of servovalve command voltage. This relation is nearly independent of contact force, from zero (out of contact) to forces approaching the saturated force capability of the axis. In this topology, the force feedback (FF) is compared to the prescribed force signal (CF) and the force error signal (FE) (i.e., the difference between these two signals) passes through a compensator 140 that acts on the force error signal. The compensator 140 converts the force error to a compensated position error (PEf) by processing the force error (FE) through a compensation function C. The compensation function may be a linear or nonlinear function according to the requirements of different prostheses and/or test regimens. The compensated position error PEf is then fed to the position controller (PC) 113, which acts to correct it. By providing a conversion of force error into position error, the compensation function allows the user of the machine to command the axis as if it were force-controlled, even though the underlying control law is position control.

Mechanical compliance is an example of a compensation function. Some compliance is always present in any physical system, as a result of elastic deformation of the components of the system, and in our implementation this inherent compliance has been found to be adequate for control purposes. In some cases, it might be desirable to augment the inherent compliance with a designed compliance, which can be made large enough to become the dominant compliance in the plant.

The same position controller 113 may be used for axes in position-command mode. In this case the position error PEp is generated as the difference between the prescribed position CP and the position measured by the position transducer PF. A mode select function 109 determines the command mode of the axis by selecting which position error is sent to the position controller.

Usually, the compensation function 140 in the impedance control topology of FIG. 3, must have at least proportional and integral action for good performance. The proportional term is the modeled or physical compliance, which converts an error in force into a change in position. Integral action is needed because in general, compliance alone cannot drive the force error to zero. For example, if the prosthesis parts are out of contact, the maximum force error is the magnitude of the commanded force, and the maximum displacement of the parts is limited to the commanded force divided by the compliance. This displacement might not be enough to bring the parts into contact, and in any case will result in a residual static error in force. The integral action of the compensator produces a velocity proportional to the force error. In the case when the parts start out of contact, the integrator will bring the parts into contact and then continue to make small adjustments until the measured force corresponds to the required force.

Impedance control of force-controlled axes is fundamental to the haptic map, as will be described next. Impedance control alone typically does not provide optimal performance in a cyclic testing regimen. The servo-controller typically is still afflicted with significant phase lag and amplitude attenuation at frequencies well within the bandwidth of the prescribed waveform. It is still a problem for the axes to react quickly enough when intermittent contact is present. Tuning of the compliance and integral gains is needed. A force compensation function 140 with integral action can in principle bring the force error arbitrarily close to zero under suitable conditions, but in practice such conditions often are not encountered. Significant force errors typically will be observed in operation, requiring some form of ILC to correct them.

The Haptic Map and Haptic Mapping System

The haptic mapping system assumes a multi-body system with kinematics that is described by a rigid-body assumption. It further assumes that the relevant dynamic interactions between bodies, i.e. the contact forces, are unique-valued and continuous functions of the displacements. Strictly speaking these two assumptions are inconsistent, because for ideally rigid bodies in contact, the contact force between the bodies as a function of displacement is discontinuous. However, many practical systems with contact interactions can be characterized as "stiff" In a stiff system, the contact forces due to displacement are unique-valued and continuous, yet the displacements are small enough that they have a negligible effect on the kinematic description of the motion of the bodies. Therefore, in such a stiff system, the assumption of rigid-body kinematics, while not strictly accurate, is nonetheless a very good approximation. In particular, prosthetic joint devices and the test waveforms used for life and performance testing typically meet these conditions. Bony biological joints also typically meet these conditions. It is important to note that not all of the deformations due to contact force necessarily occur in the regions of contact between the bodies; some deformation also occurs in, e.g., the structures used to mount and support the parts of a prosthetic device.

Because the deformation has little effect on the kinematics of the system, the deformation is independent of, or at worst weakly dependent on, the speed of the trajectory. We can slow down or speed up the waveform without affecting the locations of the contact point(s) or the amount of deformation, provided that, although we change the speed of the trajectory, we maintain the rigid body positions and corresponding applied forces prescribed by the waveform.

Figure 4:
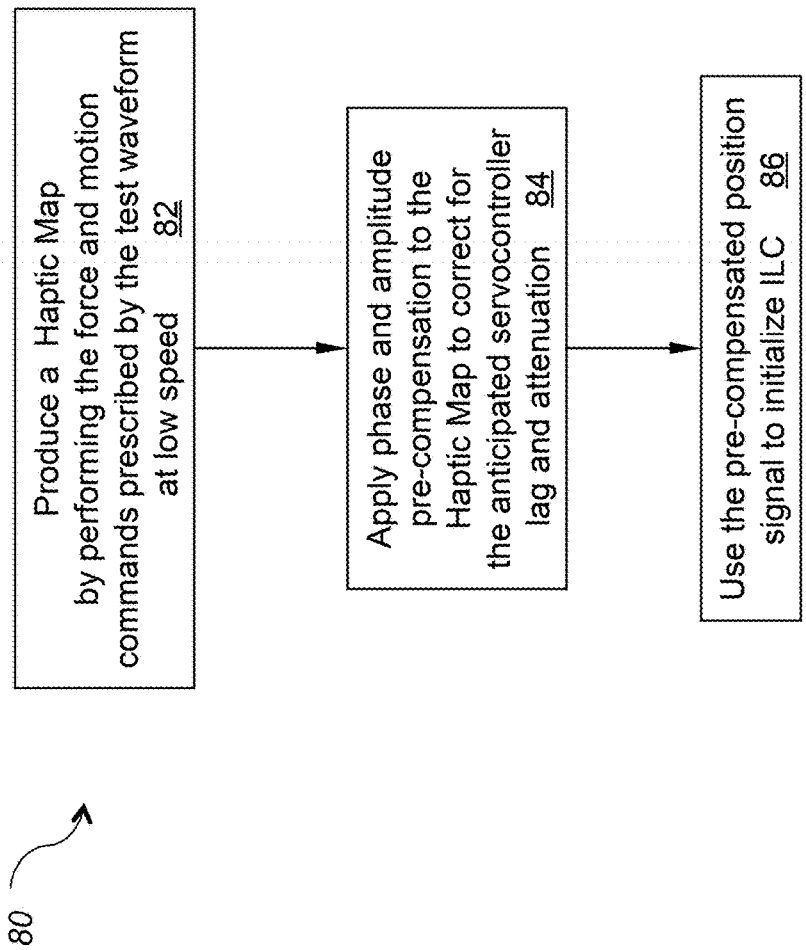
FIG. 4 is a block diagram of the haptic mapping process of this invention.

Referring to FIG. 4, the process for producing the haptic map 80 includes the following. First, we perform the force-and-motion commands prescribed by the test waveform at very low speed 82. The speed is selected to allow the servocontrollers to follow the prescribed force and displacement waveforms with minimal amplitude attenuation and phase lag. A typical speed would be in the range of 1/3 to 1/50 of the nominal speed, although other fractional speeds may be employed and will fall within the scope of the invention. In one example, a typical speed is in the range of 1/10 to 1/20 of the nominal speed. The positions of the force-controlled axes are recorded during this low-speed playback of the trajectory. This position record is the haptic map, so-called because it describes what the prosthesis "feels like" to the servocontroller.

It is important to note that the haptic map is produced without any prior knowledge or analysis of the contact conditions between the parts of the prosthesis at various relative displacement conditions. It simply records the positions of the force-controlled axes that the impedance controllers produce in order to follow the prescribed forces. No iteration is required because we excite the axis servocontrollers only in their near-DC response region. Therefore the haptic map can be produced in a reasonably short time, on the order of 10 to 20 seconds for a typical waveform. In most cases, this time will be negligible compared with the time required for the test operator to mount and set up the prosthetic device in the testing machine.

Because of the phase and magnitude characteristics of the servocontrollers, we do not use the haptic map directly. Instead, we apply the phase and amplitude compensation (PAC) 152 technique described previously (84). This pre-compensated wave is then used to initialize the ILC feed-forward for each axis (86). The use of a compensated wave causes the actual output of the axis to more closely approximate the original input, which in this case is the low-speed haptic map, when it is reproduced at a speed where the servo lag and attenuation cannot be ignored. As an implementation detail, since PAC is also required during the operation of ILC, the same software module can be used for both the initial ILC guess resulting from Haptic Mapping and the subsequent updates in response to residual position error PE. This merged signal path is suggested in the ILC block 150 of FIG. 3.

This pre-compensated haptic map provides an excellent initial guess for the ILC compensation waveform for each force-controlled axis. Although force errors still remain, they are small compared with the errors that would be observed in the absence of an initial guess for ILC compensation. The remaining errors can be measured and corrected by a known ILC algorithm. The use of a good initial guess allows ILC to remove the remaining errors rapidly, often in five to ten iterations of the ILC algorithm.

Since both the inner (force) control loop 131 and the outer (position) loop 132 ultimately generate a position error PE, iterative learning control (ILC) 150 can be applied to both loops with a largely shared software implementation. The iterative learning control algorithm (sometimes called adaptive feed forward) provides extremely accurate tracking performance with little operator adjustment. ILC relies on the cyclic nature of the control scenario. The error from the previous iteration of motion is used to improve the drive signal for the next iteration.

ILC is a form of integral gain. However, customarily integral loop gain provides a corrective signal that is proportional to the time integral of the error signal. Tracking is hampered by the fact there is an inherent lag between the application of the corrective signal and the response of the machine. If the lag is sufficiently large then the phase relationship between the corrective signal and the actuator response can approach 180 degrees. At that point positive reinforcement of the error will occur and instability will ensue. Higher loop gains compound this problem and as a result there is a limit to the integral gain that can be applied to the system, resulting in a limit to the amount of error that can be corrected.

Iterative learning control circumvents this issue by using an error measurement made during a previous iteration of the cycle which is then processed into a compensation that can be applied to a future cycle with optimal phase shift. Assuming that the error is cyclic allows the ILC system to use data from a previous cycle as a prediction of error in a future cycle, before the cycle actually occurs. This ability to anticipate the expected error allows the ILC system to compensate for the phase lags that occur in a real servo system.

Assuming that the error is both cyclic and entirely dependent on controlled inputs, then the corrective signal, generated with a phase lead that compensates for the servo's phase lag, can drive the machine's actuators closer to a perfect error free solution. If the correction technique is applied iteratively it should be possible to eliminate the control error altogether. In reality, some of the error is always caused by external disturbances, and there can be other systematic errors of measurement and calculation, so that ultimately there is always some system error that is not susceptible to correction by ILC. Nonetheless, iterative learning control has been found to be of extraordinary benefit in the control of prosthetic device simulator machines.

Effectiveness of Haptic Mapping

The value of the haptic mapping system is shown in FIG. 6A-FIG. 6E. In FIG. 6A-FIG. 6E the force command waveform 72 is identified as Force Command. FIG. 6A-FIG. 6E also show the force response measured by the force sensor 19, identified as Force Response. FIG. 6A-FIG. 6E show also the difference between the commanded and measured waveforms, identified as Force Error and plotted with a different base offset for clarity.

Figure 6C:
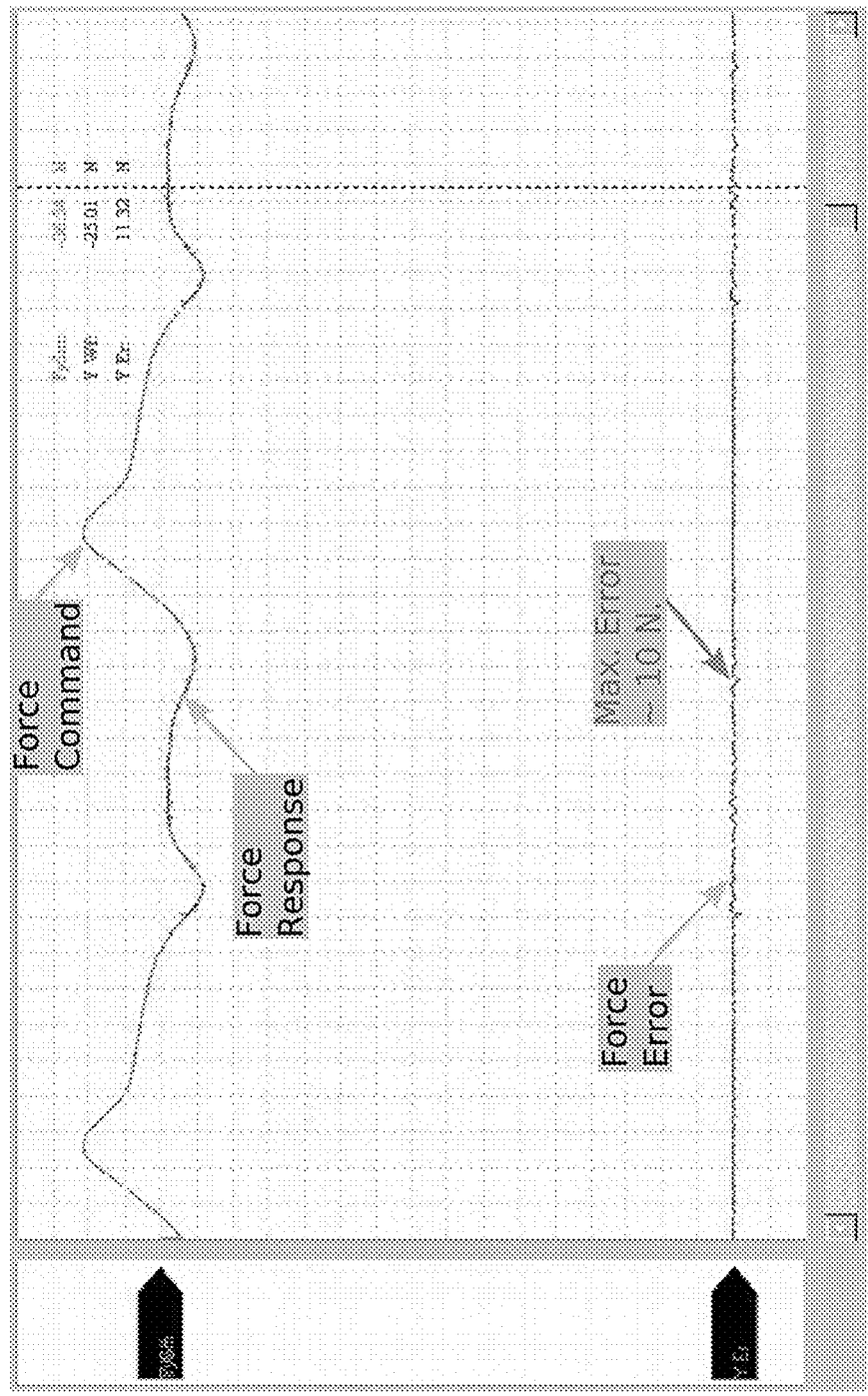
Figure 6D:
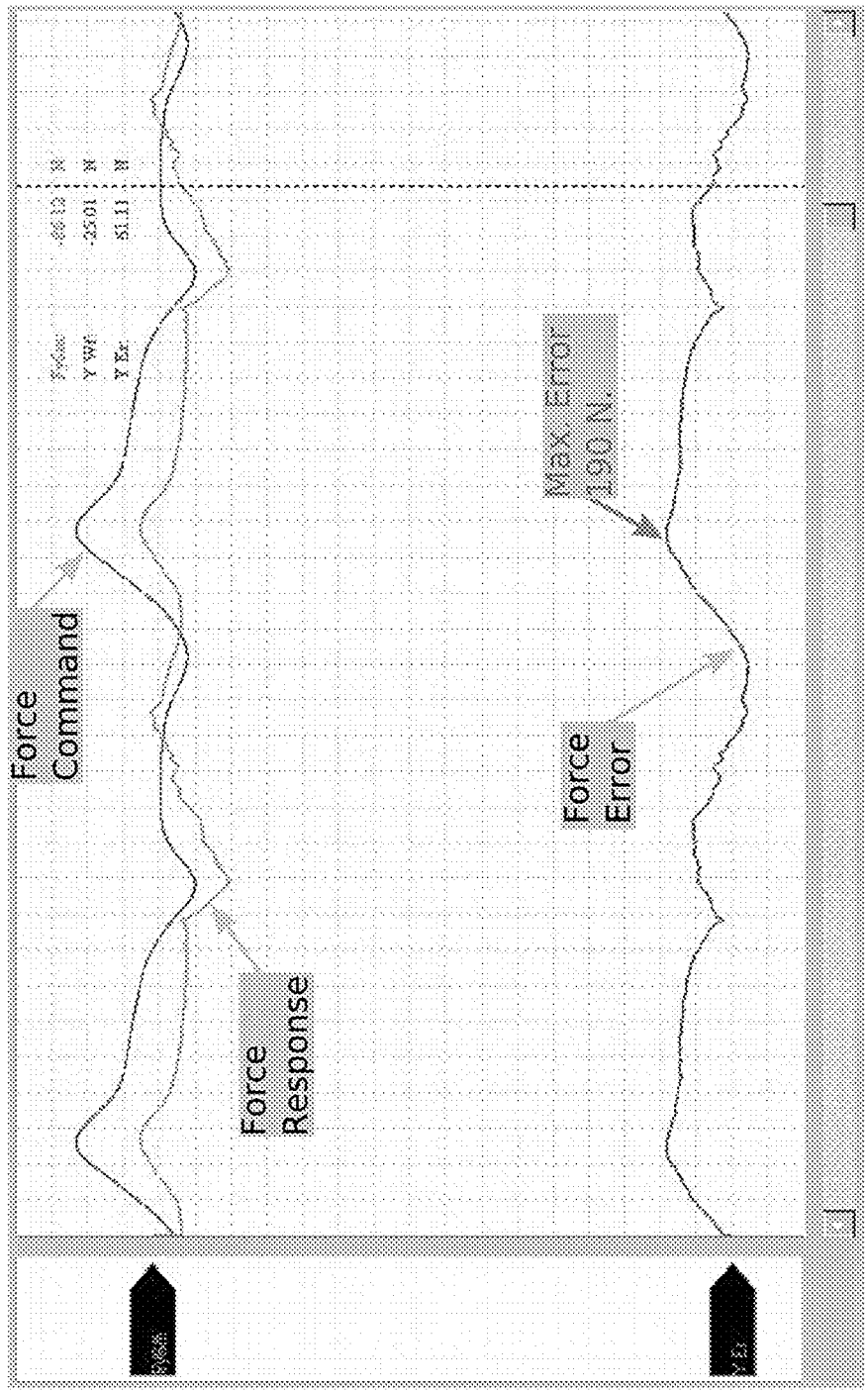
Figure 6E:
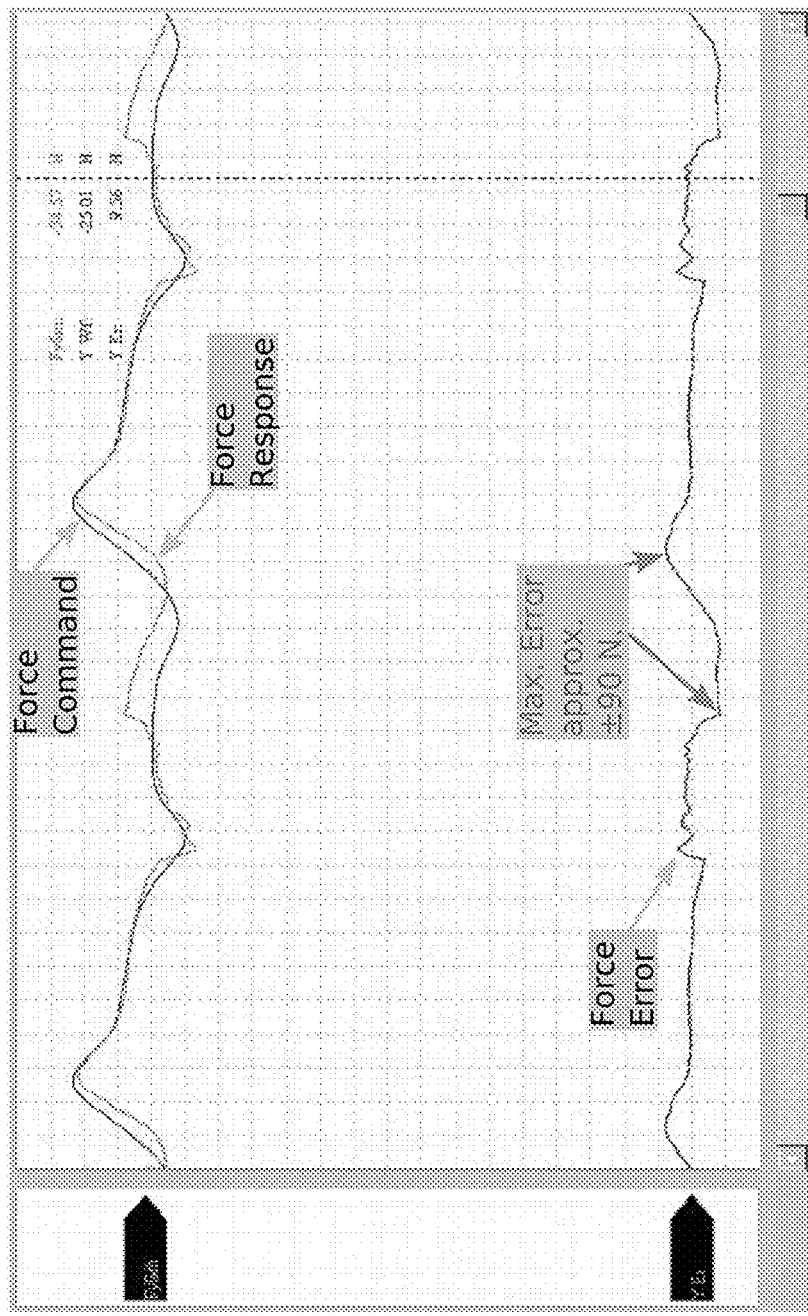

FIG. 6A shows the first two cycles of the test waveform when the waveform is started without haptic map pre-compensation. The peak error is approximately 1258 N. When the haptic map system is activated, the peak error in the first two cycles is dramatically reduced, to approximately 450 N, as shown in FIG. 6B. This level of error is still undesirably large. Therefore the previously-mentioned ILC technique is used. After several hundred cycles a result shown in FIG. 6C is obtained. The force error has been reduced to a trivially small amount, approximately ±10 N. The error still remaining is due in part to non-cyclic behavior and in part to high-frequency error that is effectively ignored by limiting the terms in the discrete Fourier transform used during PAC. Finally, FIG. 6D and FIG. 6E show the improved rate of convergence provided by the haptic map. FIG. 6D and FIG. 6E correspond to FIG. 6A and FIG. 6B after 20 cycles of the waveform have been executed. Although in both cases ILC has considerably reduced the error from the initial values, without the better initial guess provided by the haptic map, the error in FIG. 6D is still about 190 N. The reduced initial error in FIG. 6B has been further reduced after 20 waveform cycles to approximately 90 N in FIG. 6E. Therefore the haptic map system provides both improved first-cycle performance and more rapid reduction of the remaining error on subsequent cycles.

Control Systems Incorporating Haptic Mapping

Figure 5:
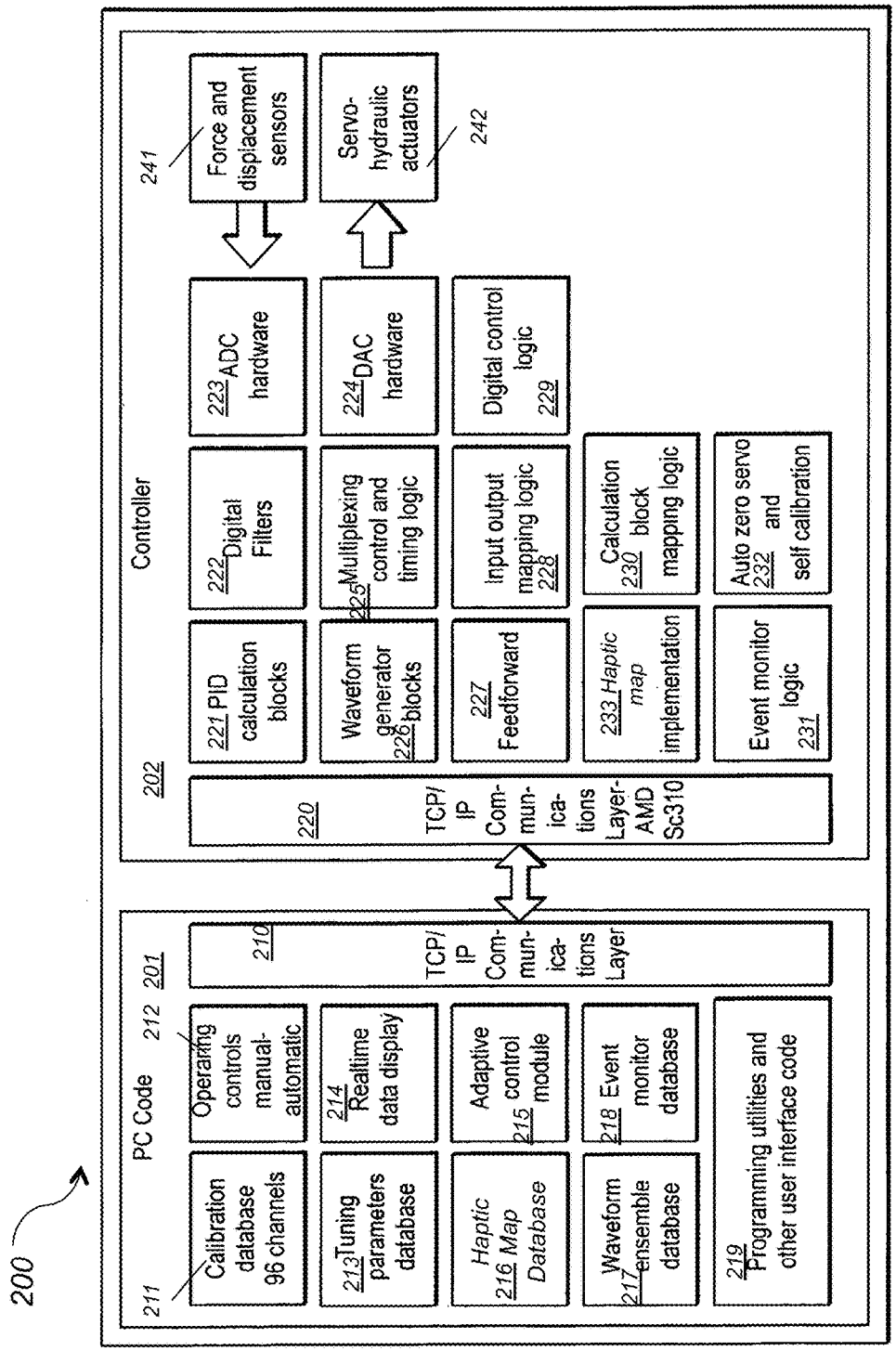
FIG. 5 is a block diagram of the various components of the control system, according to this invention.

FIGS. 3 and 5 represent in block diagram form an exemplary implementation of the hardware and software for a prosthetic joint simulator. FIG. 3 is organized along a signal-processing flow basis and the blocks indicate high-level functional units. FIG. 5 is organized around an exemplary dual-computer, multi-processor embodiment of such a controller and the blocks indicate software and/or hardware modules. The block functions identified in FIG. 3 may be split among several software modules indicated in FIG. 5.

In certain exemplary embodiments, the control system of the present invention can comprise several subsystems as illustrated schematically in FIG. 5. Software running on a PC provides the user interface 219 and manages the databases for the calibration information 211, the tuning parameters 213 including compliance parameter C, the waveform ensemble 217, the control loop tuning information 212, and the haptic map model 216. It also provides the adaptive control algorithm (iterative learning control) 215. Data and control communications between the real-time controller (RTC) 202 and PC 201 are carried over an Ethernet physical layer via TCP/IP 210. The RTC sub-system handles all the real time control and data acquisition tasks. A flexible modular arrangement of calculation and control blocks makes it possible to allocate RTC resources to optimally configure the system for different tasks and different simulator hardware scenarios. The system is designed to interface with single and multi station simulator machines, supporting up to twelve stations of control and data acquisition.

A multi-processor architecture can be used to implement the control system 202 to provide real time reliability and future extensibility. In one exemplary embodiment an industrial computer motherboard has been used to host an Intel Core 2 dual-processor CPU running a version of the Linux operating system. The motherboard is equipped with a flash memory device for storage and has a custom PCI card for communication with the off-board A/D and D/A hardware. One core of the CPU is controlled by the multi-tasking Linux scheduler and runs all tasks except the real-time controller. The tasks performed by the multitasking core include the TCP communications layer 220. The other core is reserved for exclusive and sole execution of the real-time controller task, which is not subject to interruption by the multi-tasking scheduler. In this embodiment, although the customer-facing user interface is handled by the PC 201, it is possible to include a rudimentary user interface that runs on the multi-tasking core. This user interface is useful for development and debugging. The presence of a complete Linux operating system with flash storage also allows for easy implementation of ancillary functions such as installing updated versions of the real-time code. The availability of significant floating-point computational resources permits a sophisticated control system including computation of non-linear rotational kinematics and solution of a parallel-link robotic positioning mechanism. This embodiment is easily capable of supporting a real-time servo cycle period of 500 μsec (2000 Hz) for three simulator stations with six mechanical degrees of freedom each, operating completely independently.

In a second exemplary multi-processor implementation, a low-cost single board computer with an additional I/O daughterboard is used. Again a version of the Linux operating system is installed, however a multi-processor FPGA provides a low-cost computational engine with non-symmetric multiprocessing capability. This implementation is significantly less costly than the industrial PC embodiment just discussed. However it still has adequate computational power to run up to twelve simulator stations in two independent banks of six mechanically-linked upper platforms (102) and mechanically-linked lower platforms (104) with independent Z-translation and Z-force control at each station. Again the servo cycle period in this implementation is 500 μsec.

Although the two embodiments just mentioned have significantly different performance capabilities and have been implemented in simulator machines that are optimized for different tasks, they share significant commonalities in the underlying software architecture. A modular software approach allows certain complex functional blocks to be omitted for lower-performance system requirements, with correspondingly reduced computational requirements.

The real-time controller (RTC) operates at a servo cycle rate of 2000 Hz. The complete control algorithm of every controlled channel is computed in every servo cycle. The control algorithm includes per-axis PID control (221), including force error to position error compensation 140, axis observer/estimators and feedforward compensation 227. Waveforms are generated independently for every axis by interpolation of 1024-point arbitrary waveform buffers 226. Digital filtering 222 is used on numerous signals to reduce response to out-of-band noise. General peripheral control 229 and specific timing for off-board input multiplexors 225 is performed, as well as mapping of input and output channels to specific signals 228 corresponding to the connected hardware. Force sensor taring and calibration 232 are provided. Arbitrary signals can be selected for monitoring 231 with selectable response including simple operator alert, soft stop, or instantaneous motion freeze. ADC and DAC hardware are off-board and provide the actual interfaces to hardware.

The host computer 201 is the supervisor for the real-time controller. Since safety shutdowns are handled autonomously by the RTC, under some conditions the host can program the RTC to tolerate brief interruptions of the TCP/IP link without compromising operator safety or machine integrity. The host is responsible for the ILC computations, since these inherently require computation on the record of an entire cycle's worth of data, for which the RTC is not optimized. The host provides the user-facing view of the machine, 219, 214, 212, and handles storage-intensive tasks such as the various waveform 217, calibration 211, parameter 213 and haptic map 216 databases.

The waveform ensemble for all of the controller channels is maintained in separate flat files on the host 201 which may be devised to represent different physiological functions such as walking, sitting, and stair climbing, as required by the tester. Each waveform is comprised of 1024 points representing the time sequence of force, torque, displacement or angle required to drive the machine's actuators. This database is coordinated with the configuration database and the calibration database at download time to ensure properly calibrated operation.

A utilities database maintains programmable event detection and event response information used to detect component failure and to prevent specimen damage from unforeseen overload conditions. The utilities database also maintains information for programming the start and stop behavior and transitions between waveform files.

Several embodiments of the present invention have been described. Nevertheless, it will be understood that various modifications may be made without departing from the spirit and scope of the invention. Accordingly, other embodiments are within the scope of the following claims.

What is claimed is:
1. A system for a joint testing comprising:
   a simulator stage comprising first and second mounts configured to support first and second elements of a prosthetic joint device, respectively,
   a drive system configured to apply testing forces and displacements to the first and second elements of the prosthetic joint device;
   a force sensor configured to measure forces applied to the first and second elements of the prosthetic joint device;

a displacement sensor configured to measure displacements applied to the first and second elements of the prosthetic joint device;

a digital control system configured to control the drive system in response to inputs from a test waveform, the force sensor and the displacement sensor, so that the applied testing forces and displacements on the first and second elements of the prosthetic joint device are close to prescribed testing forces and displacements, respectively; and wherein the digital control system comprises an impedance control topology, a waveform compensation system and an iterative learning control system (ILC) comprising a haptic mapping application.

2. The system of claim 1, wherein the haptic mapping application is configured to first generate a haptic map by performing force and displacement commands prescribed by the test waveform at a speed selected to allow servocontrollers to follow prescribed force and displacement waveforms with reduced amplitude attenuation and phase lag and to record positions of force-controlled axes, next to apply phase and amplitude pre-compensation to the generated haptic map to correct for anticipated drive system lag and attenuation in the recorded positions of the force-controlled axes, thereby generating a pre-compensated haptic map, and then to use the pre-compensated haptic map to initialize the ILC system.

3. The system of claim 2, wherein the haptic mapping application generates the haptic map by performing force and displacement commands prescribed by the test waveform at a speed in the range of 1/3 to 1/50 of a nominal speed.

4. The system of claim 1, wherein the waveform compensation system is configured to receive the test waveform and apply phase and amplitude compensation in order to generate a compensated waveform.

5. The system of claim 4, wherein the compensated waveform is used as an input to the drive system and comprises a modulated phase and a modulated amplitude and wherein the modulated phase and modulated amplitude of the compensated waveform compensate for a phase lag and amplitude attenuation of the drive system so that the drive system output is close to the prescribed testing forces and displacements.

6. The system of claim 1, wherein the drive system comprises one or more actuators.

7. The system of claim 6, wherein the actuators are controlled by electrically-actuated servo-valves.

8. The system of claim 1, wherein the impedance control topology comprises a multi-axis compensator and a multi-axis position controller.

9. The system of claim 8, wherein the compensator is configured to receive a force error comprising a difference between the input from the force sensor and the prescribed testing forces and to convert the force error to a compensated position error by applying a compensation function to the force error.

10. The system of claim 9, wherein the position controller is configured to receive and correct the compensated position error.

11. The system of claim 8, wherein the position controller is configured to correct a position error comprising a difference between the input from the position sensor and the prescribed displacements.

12. The system of claim 9, wherein the compensation function comprises a proportional component and an integrating component.

13. The system of claim 2, wherein the ILC is configured to receive position errors and force errors and convert them into a frequency domain representation.

14. The system of claim 1, wherein the testing forces comprise linear and/or rotational forces.

15. The system of claim 1, wherein the displacements comprise translational and/or rotational displacements.

16. A method for a joint testing comprising:
providing a simulator stage comprising first and second mounts configured to support first and second elements of a prosthetic joint device, respectively, providing a drive system configured to apply testing forces and displacements to the first and second elements of the prosthetic joint device;

providing a force sensor configured to measure forces applied to the first and second elements of the prosthetic joint device;

providing a displacement sensor configured to measure displacements applied to the first and second elements of the prosthetic joint device;

providing a digital control system configured to control the drive system in response to inputs from a test waveform, the force sensor and the displacement sensor, so that the applied testing forces and displacements on the first and second elements of the prosthetic joint device are close to prescribed testing forces and displacements, respectively; and wherein the digital control system comprises an impedance control topology, a waveform compensation system and an iterative learning control system (ILC) comprising a haptic mapping application.

17. The method of claim 16, wherein the haptic mapping application is configured to first generate a haptic map by performing force and displacement commands prescribed by the test waveform at a speed selected to allow servocontrollers to follow prescribed force and displacement waveforms with reduced amplitude attenuation and phase lag and to record positions of force-controlled axes, next to apply phase and amplitude pre-compensation to the generated haptic map to correct for anticipated drive system lag and attenuation in the recorded positions of the force-controlled axes, thereby generating a pre-compensated haptic map, and then to use the pre-compensated haptic map to initialize the ILC system.

18. The method of claim 17, wherein the haptic mapping application generates the haptic map by performing force and displacement commands prescribed by the test waveform at a speed in the range of 1/3 to 1/50 of a nominal speed.

19. The method of claim 16, wherein the waveform compensation system is configured to receive the test waveform and apply phase and amplitude compensation in order to generate a compensated waveform.

20. The method of claim 19, wherein the compensated waveform is used as an input to the drive system and comprises a modulated phase and a modulated amplitude and wherein the modulated phase and amplitude of the compensated waveform compensate for a phase lag and amplitude attenuation of the drive system so that the drive system output is close to the prescribed testing forces and displacements.

21. The method of claim 16, wherein the impedance control topology comprises a compensator and a position controller.

22. The method of claim 21, wherein the compensator is configured to receive a force error comprising a difference between the input from the force sensor and the prescribed testing forces and to convert the force error to a compensated position error by applying a compensation function to the force error.

23. The method of claim 22, wherein the position controller is configured to receive and correct the compensated position error.

24. The method of claim 22, wherein the position controller is configured to correct a position error comprising a difference between the input from the position sensor and the prescribed displacements.

25. The method of claim 22, wherein the compensation function comprises a proportional component and an integrating component.

26. The method of claim 17, wherein the ILC is configured to receive position and force errors and convert them into a frequency domain representation.

* * * * *